United States Patent [19]
Grob et al.

[11] Patent Number: 5,174,149
[45] Date of Patent: Dec. 29, 1992

[54] PROCESS AND DEVICE FOR THE VAPORIZATION INJECTION OF LIQUID SAMPLES IN GAS CHROMATOGRAPHIC ANALYSIS APPARATUSES

[75] Inventors: Konrad Grob, Firharltorf; Fausto Munari, Milan, both of Italy

[73] Assignee: Carlo Erba Strumentazione S.p.A., Italy

[21] Appl. No.: 704,366

[22] Filed: May 23, 1991

[30] Foreign Application Priority Data

Jun. 11, 1990 [IT]  Italy ............... 20605 A/90

[51] Int. Cl.⁵ ............................................. G01N 30/12
[52] U.S. Cl. .................................................. 73/23.41
[58] Field of Search ...................... 73/23.41, 23.42

[56] References Cited

U.S. PATENT DOCUMENTS

| | | | |
|---|---|---|---|
| 3,225,520 | 12/1965 | Burow | 73/23.41 X |
| 3,298,786 | 1/1967 | Hinsvark | 73/23.41 X |
| 4,704,141 | 11/1987 | Krebber | 73/23.41 X |

FOREIGN PATENT DOCUMENTS

| | | | |
|---|---|---|---|
| 3900799 | 6/1990 | Fed. Rep. of Germany | 73/23.41 |
| 486271 | 1/1976 | U.S.S.R. | 73/23.42 |
| 832398 | 5/1981 | U.S.S.R. | 73/23.41 |
| 1527546 | 12/1989 | U.S.S.R. | 73/23.41 |

Primary Examiner—Hezron E. Williams
Assistant Examiner—Joseph W. Roskos
Attorney, Agent, or Firm—Lerner, David, Littenberg, Krumholz & Mentlik

[57] ABSTRACT

The present invention relates to devices and processes for the introduction of a liquid sample into an apparatus for gas chromatographic analysis. A sample is injected into a vaporization chamber positioned upstream of a gas chromatographic column. The vaporization chamber is equipped with a means to feed a carrier gas selectively into the chamber, the chamber being kept at a temperature at least equal to the boiling temperature of the solvent at the operating pressure. A separation is effectuated between the sample and its carrier solvent, the solvent vapor is exhausted through an exhaust duct. Thereafter, the flow of carrier gas is restored to the chamber and the separated solvent is exhausted from the chamber through a separate outline into a gas chromatographic column.

21 Claims, 1 Drawing Sheet

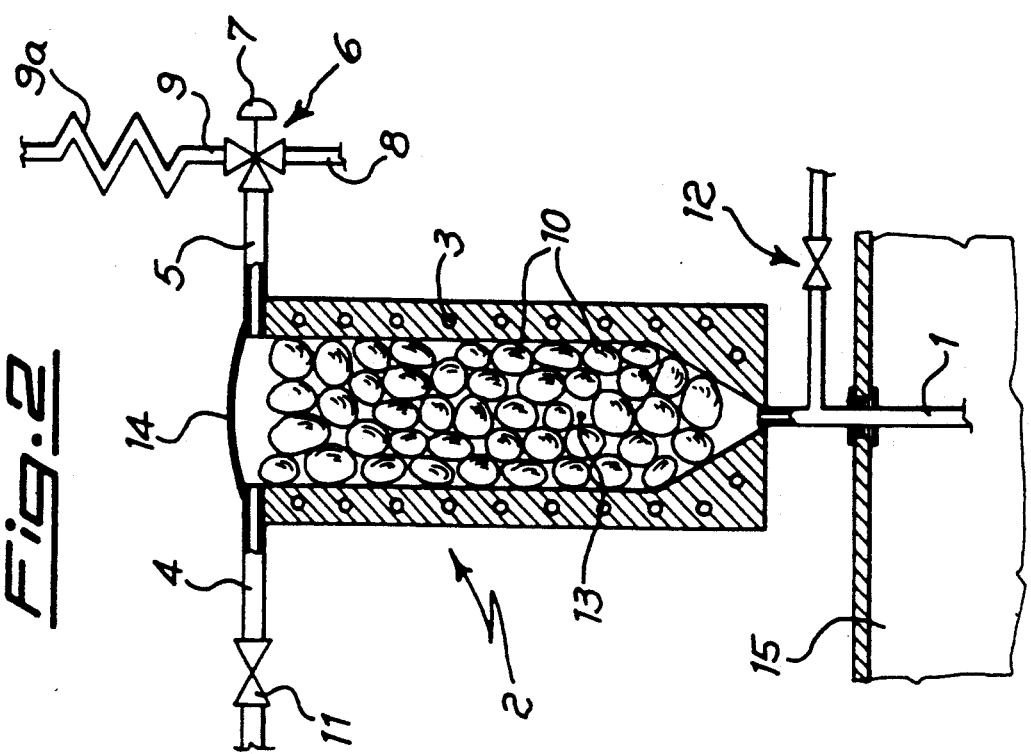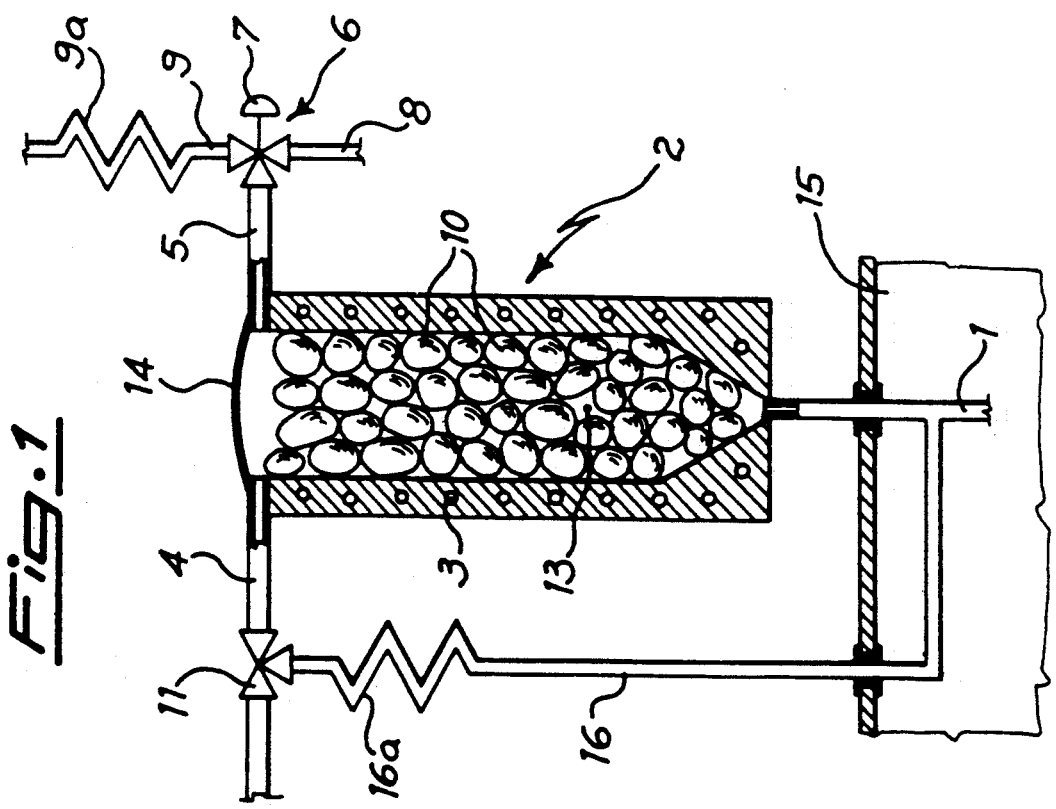

PROCESS AND DEVICE FOR THE VAPORIZATION INJECTION OF LIQUID SAMPLES IN GAS CHROMATOGRAPHIC ANALYSIS APPARATUSES

BACKGROUND OF THE INVENTION

1. Field of the Invention

This invention relates to a process and a relevant device for the introduction of liquid samples into apparatuses for gas chromatographic analysis, specially designed for samples containing high percentages of solvent and namely samples having relatively large volume, containing compounds to be analysed in very low concentrations in the relevant solvent.

As well known, the introduction of samples containing high percentages of solvent compared to the compounds to be separated involves serious problems due to the need of eliminating a considerable portion of solvent before it reaches the detector.

2. Description of the Prior Art

Several techniques of separation or splitting have been proposed, wherein only a part of the sample is fed to the detector. The latest techniques envisage to enrich the sample in the components to be analyzed, eliminating a considerable portion of the solvent alone before its introduction into the separation column.

According to said techniques, the liquid sample is injected into a vaporization "chamber" (such as for instance the "retention gap" in K. Grob et al., J. Chromatogr., 295 (1982) 15) where the liquid solvent evaporates and thus separates from the compounds. By this technique it is possible to avoid the loss of volatile compounds, but the system is sensitive to contaminations caused by high boiling compounds and water.

Another technique used is the one known as "solvent split injection", Vogt et al, in J. Chromatogr. 174 (1979) 437. If volatile compounds are present, this method presents some drawbacks, one of which in particular makes its application difficult. It is in fact necessary to accurately regulate the speed of introduction of the liquid sample into the vaporization chamber, which must be approximately the same as the speed of evaporation of the solvent, which speed on its turn depends on the exhaust flow, on the temperature and the solvent. As a matter of fact, in case the evaporation speed of the solvent is higher than that of sample feeding, even the most volatile compounds will mostly vaporize and will be discharged through the exhaust valve without being analyzed. If, on the contrary, the sample is fed to the chamber at a much higher speed than that of the solvent evaporation, some still liquid sample will remain inside the vaporization chamber, from where, after exceeding a critical volume of approximately 20 or 30 microliters, it will enter the column and the exhaust line with all the known problems involved.

It is furthermore necessary to accurately control the time for opening and closing the exhaust valve, in order to avoid both the presence of a big volume of liquids inside the injector (when the discharge duct is closed too soon) and the loss of most volatile compounds (when the discharge duct is closed too late).

It is evident how complex the regulation of discharge conditions is, even considering the impossibility of exactly measuring the flowrate of vapours in the splitting duct and their dilution in the carrier gas.

OBJECTS OF THE INVENTION

An object of the present invention is therefore that of solving the aforementioned problems by providing a process for the introduction by vaporization of liquid samples into apparatuses of gas chromatographic analysis, wherein the control of the flow of the solvent evaporated through an exhaust duct may be easily achieved even with relatively high sample volumes, reducing to the minimum the parameters to be regulated.

Another object of the invention is to provide a process of the aforedescribed type which reduces to the minimum the loss of volatile compounds during the solvent vapour evaporation and exhaust step.

Still another object of the invention is to provide a device for carrying out said process.

SUMMARY OF THE INVENTION

More particularly, the invention relates to a process for the introduction of a liquid sample, formed by components to be analyzed and by a relevant solvent, into an apparatus for gas chromatographic analyses, of the type wherein said sample is injected into a vaporization chamber positioned upstream a gas chromatographic column, provided with means to feed a carrier gas and with an outlet line, and kept at a temperature at least equal to the boiling temperature of the solvent at operating pressure, characterized in that it comprises the steps of: cutting off or significantly reducing the carrier gas flow fed to said vaporizaton chamber; introducing the sample into said chamber; evaporating at least part of the introduced sample; cause the vapours obtained to flow along at least part of said chamber, from a first injection position to a second exhaust position of said vapours; separating during said flowing along said chamber at least part of the evaporated solvent from at least part of eventual compounds evaporated therewith; exhausting at least part of the vapours reaching said second position via an exhaust duct; cutting off or partializing the flow through said exhaust duct; restoring the carrier gas feeding to said vaporization chamber and sending to said column the portion of sample remained in said chamber.

The invention furthermore relates to a device for the introduction of a sample into an apparatus for gas chromatographic analyses, of the type comprising with a vaporization chamber positioned upstream a gas chromatographic column and equipped with: means to heat it, means to feed a carried gas thereto, means to introduce a sample thereinto as well as with an outlet line coinciding or in communication with said column, characterized in that it comprises: means to cut off or partialize the carrier gas flow reaching said chamber; means to evaporate at least part of the introduced sample; means to perform an at least partial separation between solvent and compounds in the vapours thus obtained; an exhaust duct or similar means to discharge from said chamber said partially separated vapours as well as means to close or partialize said exhaust duct.

The invention will be now further described with reference to the accompanying drawings given by way of illustration.

BRIEF DESCRIPTION OF THE DRAWINGS

FIG. 1 is a schematic view in longitudinal section of an embodiment according to the invention; and FIG. 2 is a schematic view in longitudinal section of an alternative or additional embodiment with respect to that of FIG. 1.

DESCRIPTION OF THE PREFERRED EMBODIMENTS

As previously mentioned, the present invention envisages to evaporate at least part of the sample injected into the vaporization chamber in absence of carrier gas, or with a very reduced carrier gas flow. The thus generated vapours expand and flow through the chamber from the injection position, where evaporation occurs, to a second position, the exhaust position, where they escape from the chamber itself. In other words, the flow of vapours is given by the vapour pressure generated by the sample vaporization itself, and therefore vapours are discharged because of their expansion: when the vapour pressure of the evaporated sample falls down to a value approximately corresponding to the one present in the chamber before the injection, vapours do not escape any longer from said exhaust position. In this way, the regulation of the fluid flow through the exhaust duct is substantially automatic. Moreover, the presence of liquid sample and its very little diluted vapours creates a solvent effect which contributes to decrease the loss of volatile compounds during evaporation of the solvent itself.

When vapours do no longer flow through said exhaust duct, the exhaust duct is closed or partialized, the carrier gas feeding is restored and the chamber is brought to the temperature of vaporization of all sample compounds in a way as to send them into the column.

FIG. 1 is a schematic representation of a possible embodiment of a device according to the invention, where, as previously mentioned, upstream a separation gas chromatographic column there is provided a vaporization chamber 2, into which the liquid sample to be analyzed is introduced by way of known means (not shown).

The chamber 2 is provided with cooling and heating means 3, independent from the heating means of the oven 15 and the column, to keep it at a temperature which, at the operating pressure present inside said chamber, must be at least equal to the boiling temperature of the solvent, so as to cause evaporation of at least part of the introduced sample.

The chamber 2 is provided on a first side with a duct 4 for carrier gas feeding (He for instance) and with a duct 5 to discharge at least part of the resulting vapours, as well as with means 6 of type known in the technique, to control the flow of vapours therethrough, said means consisting of a valve 7 and ducts 8 and 9. The duct 4 is provided with a valve 11 or similar means to regulate the carrier gas flow to the chamber 2. As mentioned hereinabove, the carrier gas flow during the device operation will be cut off or at least reduced to a mere "purge" flow to prevent vapours from entering the duct 4. On the opposite side the chamber 2 is provided with an outlet line 1 which can be formed by the gas chromatographic column itself or by a precolumn or the like, connected to said column.

The chamber 2 is upperly closed in a known way, for instance by a septum 14 allowing for example the introduction of the injection syringe needle or the connection of a branching duct from an LC apparatus, as far as a first injection position indicated by 13.

The duct 5 constitutes said second position, the exhaust position, which is reached by the evaporated portion of sample and presents generally lower hydraulic resistance than that of the outlet line I. In this way, the vapours of the solvent and of possible volatile compounds will of course tend to escape via the duct 5 rather than along the line thus generating a flow of the evaporated sample which in the specific case of FIGS. 1 and 2 is a flow in the opposite direction to that of normal elution of carrier gas.

It is herein pointed out that the position of the duct 5 compared to the inlet of the line 1 and therefore the direction of the vapour flow in the chamber 2 are not critical; in particular said flow can also follow the normal direction of elution, provided that the vapours expanding from the injection position (where evaporation takes place) to the exhaust position come in contact with separation means to separate at least partly the solvent vapour from the other compounds evaporated therewith.

Separation means of any type suitable to obtain said at least partial separation can be used. For instance, there can be envisaged means to heat in a differential way the chamber 2 and cause condensation of the evaporated compounds before their discharge through the duct 5.

The preferential embodiment features that said separation means consist of a packing of inerts 10, of the type generally used in gas chromatography (e.g. Tenax GC ®) possibly provided with a stationary phase.

Obviously, the positions of injection 13 and discharge 5 must not be adjacent but spaced of a sufficient length to cause vapours to flow through said packing 10 and ensure an at least partial separation between the evaporated compounds and solvent. For example, the injection point 13 can be placed in the vicinity of the septum 14 and the duct 5 in the lower section of the chamber, close to the column inlet 1.

Preferably, however, as shown in FIGS. 1 and 2, the feeding point 13 is positioned in the vicinity of the area connecting said chamber 2 with the column 1, and in any case in the lower half of the chamber 2, whereas the duct 5 is located in the upper section of the chamber.

In order to introduce the sample at a not strictly controlled speed, and in particular to be able to inject it at higher speed than that of evaporation of same, so as to have inside the chamber the liquid sample required to obtain the desired solvent effect, the invention also envisages that inside the chamber 2 there are provided means to physically hold the liquid sample not immediately evaporated after its introduction and thus preventing it from penetrating the outlet line 1.

In the preferred embodiment as shown, said holding means are advantageously in the form of said packing of inerts 10 that thus serve both as means of partial separation of vapours and as holding means of the liquid sample.

In this way the sample can be introduced at a speed higher than the evaporation speed and whose maximum only depends on the ratio between sample volume and free volume of chamber 2, where "free volume" means the difference between the chamber volume and the volume of the packing or corresponding means present in the chamber 2. More in particular, if the volume of sample to be introduced is lower than the chamber free volume, it will not be necessary to control the sample introduction speed. Otherwise it will on the contrary be necessary to control said introduction speed which can be in any case higher than the maximum speed of the solvent evaporation.

In the shown preferred embodiment, the exhaust duct 5 can be alternatively connected, by way of valve 7, to said duct 8 which can be on its turn connected to a source of reduced pressure (not shown), or to a purge duct 9, equipped with a partializing resistence 9a. The use of a reduced pressure, together with the chamber 2 heating, causes evaporation of at least part of the introduced liquid sample and simultaneously avoids the passage of the evaporated sample to the line 1.

On the contrary, in case the vaporization chamber is kept at atmospheric pressure, the line is kept at a sufficiently high temperature as to prevent any recondensation of the sample vapours entered therein. This does not prevent vapours from flowing in the line 1, but avoids that recondensation causes a local fall down of pressure which would call other vapours from the chamber, which on their turn would recondensate, and so on, entering the line or column 1.

If possible, the column temperature is preferably set at a value of approximately 60-90 degrees C below the elution temperature of the first peak of interest, so as to allow to make up again the bands of evaporated compounds, which have entered the column during the initial analysis step, according to the method known as "cold trapping".

In addition to the aforedescribed means, the invention can provide a branching 16 which connects the duct 4 with the line downstream the vaporization chamber, to feed a reduced flow of carrier gas to the chamber 2 in a direction opposite to that of the normal elution of the evaporated sample.

In this case there are provided known means of partialization of the carrier gas flow along the branching line 16, such as for instance resistance 16a as shown in FIG. 1 or an electrovalve (not shown). FIG. 2 shows also traditional splitting means 12 placed at the beginning of the gas chromatographic column for splitting the sample tail when required.

During operation, first of all the valve means is actuated to cut off or substantially limit the carrier gas flow to the chamber 2. A limited flow of said gas may be foreseen with the purpose of preventing vapours from entering the duct 4.

Then the chamber 2 is brought to the desired temperature, namely to a temperature at least corresponding to the boiling temperature of the solvent at operating pressure, that is at the pressure present inside the chamber. If necessary or desired, said pressure is kept at a lower value than the ambient one connecting the chamber with said vacuum source through the duct 8.

The line or column 1 is brought to a second desired temperature, selected according to what previously described, by means of the oven 15

The sample is then introduced at a speed selected according to what previously described. This means that it is in any case possible that the introduction speed is higher than the maximum speed of evaporation, in that the packing of inerts 10 holds part of the non evaporated liquid and thus ensures higher flexibility of the injection parameters. Contrary to the known processes, even lower speeds are perfectly acceptable.

During the sample introduction, part of it starts to evaporate: the evaporation, which goes on even after the sample introduction is over, leads to an expansion of the gases coming out (practically overflowing) from the duct 5. Because of the difference of fluid resistance between the duct 5 and column 1, most vapours leaving the chamber 2 escape from duct 5 rather than from line 1 and anyway, in case of evaporation at reduced pressure, there will be no passage of vapours to the line 1.

During this flowing along the chamber 2 of the solvent and the most volatile compounds evaporated therewith, the compounds are mostly held by the packing of inerts 10 and/or condensate in the coldest areas of the chamber 2; a portion of at least partially separated vapours reaches the duct 5 and is exhausted via means 6.

Once a sufficient amount of solvent vapours has been exhausted, the pressure of the vapours present inside the chamber falls to operating values, the exhaust duct 5 is closed or partialized by the valve 7, the carrier gas flow is restored and the temperature of the chamber 2 is brought to normal values of vaporization and passage of the sample (that is of the compounds and the solvent remained) to the outlet line 1.

Preferably, a small purge flow is maintained through the duct 9 of the exhaust means in order to avoid possible backward ejection of vapours from the duct 5 to the chamber 2.

In the latter stage, therefore, the flow of the vaporized sample follows the normal elution flow along the column 1, and the bands of partially separated compounds which had formed along the packing 10 and/or the chamber 2 walls are thus at least partly recombined before their entering the column 1, wholly beneficial to analytical resolution.

The following tables 1 and 2 report the maximum evaporation speeds experimentally obtained, at an operating pressure equal to the ambient one and at a reduced operating pressure, respectively, and using as vaporization chamber glass tubes with an inner diameter of 5 and 2 mm and a length of 7 cm packed with Tenax GC ® or Chromosorb G ® (for vaporization at reduced pressure). The chamber was thermostated in a silicon oil bath; the capillary column presented at the outlet an inner diameter of 0.32 mm and the exhaust duct an inner diameter of 0.53 mm.

TABLE 1

| Solvent | Temperature | Internal diameter mm | Vaporization speed ($\mu$l/min) |
|---|---|---|---|
| Diethyl ether | 85 | 5 | 600 |
| Methanol | 95 | 5 | 130 |
| Methanol | 90 | 2 | 80 |
| Water | 125 | 5 | 50 |
| n-Hexane | 100 | 5 | 450 |
| n-Hexane | 100 | 2 | 300 |

TABLE 2

| Solvent | Temperature | Internal diameter mm | Vaporization speed ($\mu$l/min) |
|---|---|---|---|
| n-Hexane | 55 | 5 | 600 |
| n-Hexane | 45 | 5 | 500 |
| n-Hexane | 45 | 2 | 200 |
| Chloroform | 60 | 2 | 400 |
| Methanol | 45 | 2 | 100 |
| Methanol | 60 | 2 | 150 |
| Water | 85 | 2 | 80 |
| Water | 65 | 2 | 40 |

We claim:

1. A process for the introduction of a liquid sample dissolved in a liquid solvent into an apparatus for gas chromatographic analysis comprising the steps of:
providing a vaporization chamber positioned upstream of a gas chromatographic column, said vaporization chamber including a gas feeding duct, an outlet line, and an exhaust duct;

feeding a carrier gas into said vaporization chamber through said gas feeding duct;

maintaining the temperature within said vaporization chamber at a temperature at least equal to the boiling temperature of said solvent at operating pressure;

cutting off or significantly reducing the flow of carrier gas feeding into said vaporization chamber through said gas feeding duct;

introducing said sample dissolved in said solvent into said vaporization chamber at a first injection position within said vaporization chamber;

evaporating at least part of said liquid solvent whereby vapors obtained from said evaporating liquid solvent are caused to flow from said first injection position toward said exhaust duct, thereby separating at least a part of said solvent from said sample;

exhaust from said vaporization chamber through said exhaust duct at least a part of said solvent vapors;

cutting off or significantly reducing the flow of said exhausting solvent vapors through said exhaust duct; and restoring said flow of carrier gas feeding into said vaporization chamber through said gas feeding duct and displacing said sample from said vaporization chamber into said gas chromatographic column through said outlet line.

2. The process of claim 1 wherein said liquid sample dissolved in said liquid solvent is introduced into said vaporization chamber at a rate which is higher than the rate of evaporation of said liquid solvent.

3. The process of claim 2 further comprising the step of holding said liquid sample on a physical means positioned inside said vaporization chamber.

4. The process of claim 3 wherein said physical means is a packing disposed in said vaporization chamber which is disposed such that at least part of said liquid sample is retained on a surface of said packing and said evaporated solvent vapors are caused to flow through said packing.

5. The process of claim 1 wherein said introduction speed is regulated as a function of the free volume of said chamber and the volume of said liquid solvent to be introduced.

6. The process of claims 1, 2 or 3 wherein said first injection position is disposed adjacent said outlet line and said outlet line and said exhaust duct are remote from one another.

7. The process of claim 6 wherein said solvent vapor flows in a direction from said first injection position to said exhaust duct which is substantially opposite to the direction said carrier gas flows when feeding into said vaporization chamber through said gas feeding duct toward said outlet line.

8. The process of claim 1 wherein said solvent vapor flows in a direction from said first injection position to said exhaust duct which is substantially opposite to the direction said carrier gas flows when feeding into said vaporization chamber through said gas feeding duct toward said outlet line.

9. The process of claim 1 wherein said vaporization chamber is maintained at a pressure equal to or greater than the environmental pressure.

10. The process of claim 1 further comprising the step of introducing a flow of carrier gas into said vaporization chamber through said outlet line prior to the step of cutting off or significantly reducing the flow of said exhaust vapors through said exhaust duct.

11. The process of claim 1 further comprising the step of heating said vaporization chamber at a temperature which is sufficient to vaporize said sample therein while cutting off or significantly reducing the flow of said exhaust vapor though said exhaust duct or thereafter.

12. The process of claims 1, 2 or 3 wherein said operating pressure is less than atmospheric pressure.

13. The process of claims 1, 2 or 3 further comprising the step of maintaining said gas chromatographic column at a temperature higher than the temperature of recondensation of said sample vapors.

14. A device for introducing a liquid sample dissolved in a liquid solvent into an apparatus for gas chromatographic analysis comprising: a vaporization chamber including means to feed carrier gas into said vaporization chamber, heating means for heating the vaporization chamber, an outlet line communicating with a column of a gas chromatography, an exhaust duct from said chamber to exhaust vapors from said chamber and means to cut off or significantly reduce the flow through said exhaust duct, means to introduce a liquid sample dissolved in a liquid solvent into said vaporization chamber, means to cut off or significantly reduce the flow of carrier gas into said vaporization chamber and means to perform at least a partial separation of said solvent and said sample.

15. The device of claim 14 further comprising means disposed within said vaporization chamber to temporarily hold inside said vaporization chamber said introduced liquid sample.

16. The device of claim 14 or 15, wherein said means to perform at least a partial separation and said means to temporarily hold are packings housed inside said vaporization chamber.

17. The device of claim 16, wherein said packings include a stationary phase.

18. The device of claims 14 or 15, wherein said exhaust duct is connected to a vacuum source to maintain subatmospheric pressure inside said vaporization chamber.

19. The device of claim 14 wherein said outlet line is connected to a source of carrier gas to feed into said vacuum chamber therethrough.

20. The device of claim 14 wherein said means to introduce a liquid sample dissolved in a liquid solvent into said vaporization chamber is disposed generally adjacent said outlet line and remote from said exhaust duct.

21. A process for the introduction of a liquid sample dissolved in a liquid solvent into an apparatus for gas chromatographic analysis comprising the steps of:

providing a vaporization chamber positioned upstream of a gas chromatographic column, said vaporization chamber including a gas feeding duct and outlet line and an exhaust duct, introducing a liquid sample dissolved in a liquid solvent into said vaporization camber, evaporating and expelling said solvent from said vaporization chamber through said exhaust duct and introducing said sample into said gas chromatographic column through said outlet line.

* * * * *

UNITED STATES PATENT AND TRADEMARK OFFICE
CERTIFICATE OF CORRECTION

PATENT NO. : 5,174,149
DATED : December 29, 1992
INVENTOR(S) : Grob et al.

It is certified that error appears in the above-identified patent and that said Letters Patent is hereby corrected as shown below:

Column 5, line 39, after "means", insert --11--.
Column 7, line 19, "exhaust" should read --exhausting--.

Signed and Sealed this

Twenty-sixth Day of October, 1993

Attest:

BRUCE LEHMAN

Attesting Officer

Commissioner of Patents and Trademarks